(12) United States Patent
Davies et al.

(10) Patent No.: US 7,278,424 B1
(45) Date of Patent: *Oct. 9, 2007

(54) MEDICAMENT CARRIER

(75) Inventors: Michael Birsha Davies, Ware (GB); James William Godfrey, Ware (GB); Sylvia Maria Haglund, Oxford (GB); Paul Kenneth Rand, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/031,637

(22) PCT Filed: Apr. 19, 2000

(86) PCT No.: PCT/EP00/03515

§ 371 (c)(1),
(2), (4) Date: Dec. 19, 2001

(87) PCT Pub. No.: WO00/64778

PCT Pub. Date: Nov. 2, 2000

(30)  Foreign Application Priority Data

Apr. 24, 1999 (GB) .................................. 9909354.4

(51) Int. Cl.
A61M 15/00 (2006.01)
B65D 75/28 (2006.01)
(52) U.S. Cl. ..................... 128/203.15; 128/203.21; 221/22; 206/484; 206/438

(58) Field of Classification Search ........... 128/200.14, 128/203.21, 203.15; 53/412, 416, 422, 476, 53/477, 482, 485, 222, 232; 206/400, 411, 206/222, 820, 484; 220/279; 221/25, 27, 221/69, 70, 71; 428/198
See application file for complete search history.

(56)  References Cited

U.S. PATENT DOCUMENTS

| 103,012 | A | 5/1870 | Button |
| 776,649 | A | 12/1904 | Dumont et al. |
| 895,527 | A | 8/1908 | Williams |
| 1,192,859 | A | 8/1916 | Canfield |
| 1,476,682 | A | 12/1923 | Beckmann |
| 1,490,529 | A | 4/1924 | Dittgen |
| 2,197,845 | A | 4/1940 | Ward |
| 2,298,451 | A | 10/1942 | Balthaser |
| 2,399,000 | A | 4/1946 | Carroll |
| 2,465,879 | A | 3/1949 | Hornung |
| 2,598,823 | A | 6/1952 | O'Grady |
| 2,889,958 | A | 6/1959 | Ekenstam et al. |

(Continued)

FOREIGN PATENT DOCUMENTS

EP 0 101 298 A 2/1984

(Continued)

*Primary Examiner*—Justine R. Yu
*Assistant Examiner*—Shumaya B. Ali
(74) *Attorney, Agent, or Firm*—James P. Riek

(57)  ABSTRACT

There is provided a carrier comprising an elongate strip (10) having a first portion and a second portion; a fold between said first portion and said second portion such that the first portion contacts the second portion; and a join between the first portion and the second portion, wherein said join and the fold form the edges of a pocket or pouch (20) for containment of product. The carrier is suitable for the containment of a range of different products, particularly medicaments.

38 Claims, 5 Drawing Sheets

U.S. PATENT DOCUMENTS

| | | | |
|---|---|---|---|
| 2,968,396 A | 1/1961 | Pratt | |
| 2,989,212 A | 6/1961 | Ekenstam et al. | |
| 3,039,652 A | 6/1962 | Ekenstam et al. | |
| 3,107,782 A | 10/1963 | Jaroff et al. | |
| 3,301,392 A | 1/1967 | Regan, Jr. | |
| 3,338,400 A | 8/1967 | Edgworth et al. | |
| 3,342,326 A | 9/1967 | Zackheim | |
| 3,482,733 A | 12/1969 | Groves | |
| 3,692,176 A | 9/1972 | Templeton et al. | |
| 3,698,549 A * | 10/1972 | Glassman | 206/440 |
| 3,724,651 A | 4/1973 | Link | |
| 3,856,142 A | 12/1974 | Vassalo | |
| 3,967,761 A | 7/1976 | Melton et al. | |
| 4,274,550 A * | 6/1981 | Feldstein | 221/71 |
| 4,373,631 A | 2/1983 | Friese et al. | |
| 4,402,696 A * | 9/1983 | Gulko | 424/448 |
| 4,428,709 A | 1/1984 | Peters | |
| 4,444,310 A | 4/1984 | Odell | |
| 4,474,349 A | 10/1984 | Loeckle | |
| 4,762,124 A | 8/1988 | Kerch et al. | |
| 4,781,696 A | 11/1988 | Moulding et al. | |
| 4,884,719 A | 12/1989 | Levine et al. | |
| 4,913,311 A | 4/1990 | Garcia | |
| 4,998,621 A * | 3/1991 | Meehan | 206/466 |
| 5,011,017 A | 4/1991 | Giesen | |
| 5,077,104 A | 12/1991 | Hunt | |
| 5,239,991 A | 8/1993 | Chawla et al. | |
| 5,411,168 A | 5/1995 | Mertens et al. | |
| 5,511,689 A | 4/1996 | Frank | |
| 5,533,505 A | 7/1996 | Kallstrand et al. | |
| 5,590,645 A | 1/1997 | Davies et al. | |
| 5,660,169 A | 8/1997 | Kallstrand et al. | |
| 6,024,732 A | 2/2000 | Samuelsson | |
| 6,059,112 A | 5/2000 | Dykstra et al. | |
| 6,085,936 A | 7/2000 | Friar et al. | |
| 6,163,288 A * | 12/2000 | Yoshizawa | 341/144 |
| 6,286,507 B1 | 9/2001 | Jahnsson | |
| 6,568,533 B1 * | 5/2003 | Tanaka et al. | 206/484 |
| 6,929,004 B1 * | 8/2005 | Bonney et al. | 128/203.15 |

FOREIGN PATENT DOCUMENTS

| | | |
|---|---|---|
| FR | 850 597 A | 12/1939 |
| WO | WO88 10219 A | 12/1988 |

* cited by examiner

MEDICAMENT CARRIER

The present invention relates to a carrier for carrying a range of different products. In particular, it relates to a medicament carrier for use in an inhalation device to enable administration of medicament to a patient.

Individual or unit carriers are employed across many different industries to package, present and deliver a range of products to customers or users. Thus, for example, carriers containing unit quantities of food, beverage and toiletries are commonly sold in supermarkets. Other examples include electrical, photographic and printing products where there is again the need to package individual items to meet consumer demands. In general, such carriers must provide a clean, durable, dust-free environment to protect the product while at the same time offering easy accessibility for the consumer at low cost.

It is an object of the present invention to provide a carrier comprising a single elongate strip which offers significant benefits over existing carriers in terms of ease of use together with simplicity and cost of manufacture.

Inhalation devices are known for use with blister packs in which the medicament is held in powder form in the blisters thereof. Such packs are typically comprised of two separate entities, one of which is suitably formed to define the medicament pocket and the other is hermetically sealed to the first to form the medicament carrier. Known blister packs generally include a puncturing member, which punctures each blister in turn thus enabling the medicament to be inhaled therefrom. Generally release of the medicament dose is by puncture or rupture of the second entity. Such packs suffer from the disadvantage that they may be difficult to use, particularly as the dose releasing means may comprise one or more elongate members, such as cords or tapes, which are separately attached to films used to seal the medicament pockets. The present invention provides advantages over such packs in that it is especially useful for the elderly and infirm since the free end of the strip is readily identifiable and simple to grasp, without the added complication of numerous cords or tapes which act as a separate release mechanism.

It is an object of the present invention to provide a simple means of accessing a unit dose of medicine for inhalation, oral or topical administration by a patient or health care professional.

It is a further object of the present invention to reduce the risk of patient and/or health care professional contamination when administering a medicament, either orally or topically. For example, accessing existing trans-dermal patches or oral preparations from their carriers may result in small quantities of medicament accidentally coming into contact with the patient's or nurse's skin, thereby reducing the effective dose and posing unnecessary risks for the health care professional. The present invention seeks to address this problem by facilitating the ease with which such carriers are accessed.

A further object of the present invention is to provide a medicament carrier for use in combination with an inhalation device, wherein the free end of the strip is peeled back automatically by virtue of a releasing means incorporated into the inhalation device, hence avoiding the need to grasp the strip manually. Such a feature further enhances the ease of use of the inhalation device since minimum force is required by the user to peel back the medicament pouch.

It is also an object of the present invention to provide a medicament carrier for use in combination with an inhalation device, wherein the design of the inhalation device has the potential, if desired, to handle a medicament carrier having a large number of discrete unit doses without the device becoming unacceptably large. The present invention is particularly suitable for such use, as will be shown in embodiments, because the individual medicament containers have the ability to lie flat against the elongate strip thus forming a compact series of medicament containers.

Another advantage provided by the present invention is that the use of the flat medicament container allows air to pass over the whole container surface when opened thereby improving drug removal. The design of the carrier has the further advantage that it reduces drug loss, caused by drug adherence to the top of conventional carriers when these are discarded on opening the carrier, by making all of the drug available for delivery to the patent.

It is an additional object of the present invention to provide a simple means of packaging, presenting and accessing a variety of non-medical products, including food, beverages, disinfectants, toiletries, electrical, photographic and printing products, as will be shown in the embodiments described herein.

According to one aspect of the present invention there is provided a carrier comprising an elongate strip having a first portion and a second portion; a fold between said first portion and said second portion such that the first portion contacts the second portion; and a join between the first portion and the second portion, wherein said join and the fold form the edges of a pocket or pouch for containment of medicament, the pocket or pouch containing a unit dose of medicament therein.

In one aspect there is provided a carrier wherein the pocket or pouch comprises folds therein. In another aspect, the pocket or pouch comprises contours or ridges therein.

In another aspect, there is provided a carrier additionally comprising a retainer within the pocket or pouch for retaining medicament thereon. The retainer is for example, a mesh or sponge.

In a further aspect, each of the ends of the elongate strip has a non self-binding adhesive portion allowing reversible contact therebetween. Preferably each of the ends of the elongate strip has a peelable cover thereon. More preferably, removal of the peelable cover reveals an adhesive portion on each of the ends of the elongate strip. Most preferably, the adhesive portion enables attachment of the carrier to mammalian skin. Thus the carrier can be directly applied to the skin to administer medicament to the patient thereby providing a simplified system for topical treatments with medicament and minimal risk of contamination or loss of medicament through non-target contact.

In one aspect, there is provided a carrier comprising at least one further join forming at least one further pocket or pouch for containment of medicament.

In a further aspect, there is provided a carrier wherein the ends of the elongate strip is form a pair of pull release tabs. Preferably each of the pull release tabs is shaped for ease of grip. More preferably, each of the pull release tabs has a looped end. Most preferably, each of the pull release tabs has at least one perforation therein.

In another aspect, there is provided a carrier additionally comprising a drawstring opening mechanism. Preferably the carrier comprises protruding release ends of the drawstring for opening thereof.

In a further aspect, there is provided a carrier in multi-unit form comprising a series arrangement of a plurality of carriers as described above. Preferably each of the carriers is connected together. More preferably, each of the plurality of carriers is formable from the same elongate strip. Most preferably, the strip has a point of weakness between each carrier in the series arrangement. Suitably, each pocket or pouch is foldable to lie flat alongside the elongate strip.

In one aspect, there is provided a carrier wherein the elongate strip is flexible. Preferably the elongate strip comprises material selected from the group consisting of metal foil, an organic polymeric material and paper. More preferably, the strip comprises a laminate.

In another aspect, there is provided a carrier wherein the join is formable by a joining method selected from the group consisting of heat, laser, radio frequency, adhesive, staple, stamp, pressure and ultrasonic sealing. Suitably the join is peelable to enable peelable access to the pocket or pouch.

Preferably the medicament is in dry powder, tablet, liquid, paste, cream or capsular form. More preferably the medicament is selected from the group consisting of albuterol, salmeterol, ipratropium bromide, fluticasone propionate and beclomethasone dipropionate and salts or solvates thereof and any mixtures thereof.

According to another aspect of the present invention, there is provided an inhalation device comprising a housing in combination with a medicament carrier as described above. Preferably the inhalation device comprises a release mechanism and the carrier comprises a pair of pull release tabs connected to the release mechanism. More preferably, the release mechanism is separable from the housing of the inhalation device.

According to a further aspect of the present invention, there is provided a method of making a carrier comprising forming a fold between a first portion and second portion of an elongate strip such that the first portion contacts the second portion; forming a join between the first portion and the second portion wherein the join and the fold form the edges of an open pocket or pouch for containment of medicament; filling the open pocket or pouch with the unit dose of medicament; and closing the open pocket or pouch by forming a further join.

Preferably there is provided a method of making a carrier in multi-unit form comprising successive iterations of the method described above to form a series arrangement of a plurality of carriers.

According to another aspect of the present invention, there is provided a method of opening a carrier as described above comprising pulling the pair of pull release tabs in order to enable access to the pouch.

In a further aspect of the present invention, there is provided the use of a carrier, as described above, for dispensing medicament. Preferably the use of the carrier is for applying medicament to skin. More preferably, the use is for the treatment of cuts, abrasions or infections of skin. Optionally, the use is for dispensing slow-release formulations of medicaments via the skin.

In a preferred aspect, the medicament is used in the treatment of respiratory disorders. More preferably the medicament is used in the treatment of asthma. Most preferably the medicament is salbutamol or albuterol.

In one aspect, there is provided a carrier comprising a toiletry therein. Preferably the toiletry is selected from the group consisting of toothpaste, soap, mouthwash, shampoo, skin and face cream.

In another aspect, there is provided a carrier comprising a cleanser therein. Preferably the cleanser is selected from the group consisting of soap, detergent, enzymic preparation and organic solvent.

In a further aspect, there is provided a carrier comprising a disinfectant therein. Preferably the disinfectant is selected from the group consisting of sterilant, antiseptic and bleach.

In another aspect, there is provided a carrier comprising a light-sensitive material therein. Preferably the light-sensitive material comprises a photographic film.

In yet another aspect, there is provided a carrier comprising a marking material therein. Preferably the marking material is selected from the group consisting of toner, ink, dye, pigment, acid and alkali.

In one aspect, there is provided a carrier comprising a covering material therein. Preferably the covering material is selected from the group consisting of paint, pigment, dye, corrosion inhibitor, electrical conductor, electrical insulator and static inhibitor.

In a further aspect, there is provided a carrier comprising a toy therein. Preferably the toy is selected from the group consisting of model, figure, doll, animal, jigsaw and game.

In another aspect, there is provided a carrier comprising haberdashery therein. Preferably the haberdashery is selected from the group consisting of button, bobbin, needle, pin, eye, hook and fastener.

In one aspect, there is provided a carrier comprising a tool therein. Preferably the tool comprises a domestic tool. More preferably, the domestic tool is selected from the group consisting of can opener, bottle opener, ring-pull opener, scissors, knife, fork and spoon.

Optionally the tool comprises a home maintenance tool. Preferably the home maintenance tool is selected from the group consisting of nail, screw, pin, wire, screwdriver, knife, brush, spanner, ruler and marker.

In another aspect, there is provided a carrier comprising stationery therein. Preferably the stationery is selected from the group consisting of pencil, pen, ruler, crayon, eraser, marker, stencil, protractor, compass and paper.

In a further aspect, there is provided a carrier comprising an adhesive therein. Preferably the adhesive bonds materials selected from the group consisting of paper, plastic, wood, rubber, glass and metal.

In one aspect, there is provided a carrier comprising an agrochemical therein. Preferably the agrochemical is selected from the group consisting of herbicide, insecticide, fungicide, rodentocide, nematocide, acaracide and plant growth regulator.

In another aspect, there is provided a carrier comprising a plant seed therein. Preferably the seed is derived from plants selected from the group consisting of monocotyledonous and dicotyledonous plants.

In a further aspect, there is provided a carrier comprising a contraceptive therein. Preferably the contraceptive is either a contraceptive device or a contraceptive drug. Preferably the contraceptive device is selected from the group consisting of condom, diaphragm, sponge and coil. Preferably the contraceptive drug is selected from the Preferred embodiments of the medicament carrier according to the present invention will now be described with reference to the accompanying drawings in which.

Although reference is made solely to a pouch in the following description, similar embodiments of the present invention also apply to pockets; a pouch is herein considered an essentially closed container, whereas a pocket is an enclosed space having an opening thereto.

Figure 1A:
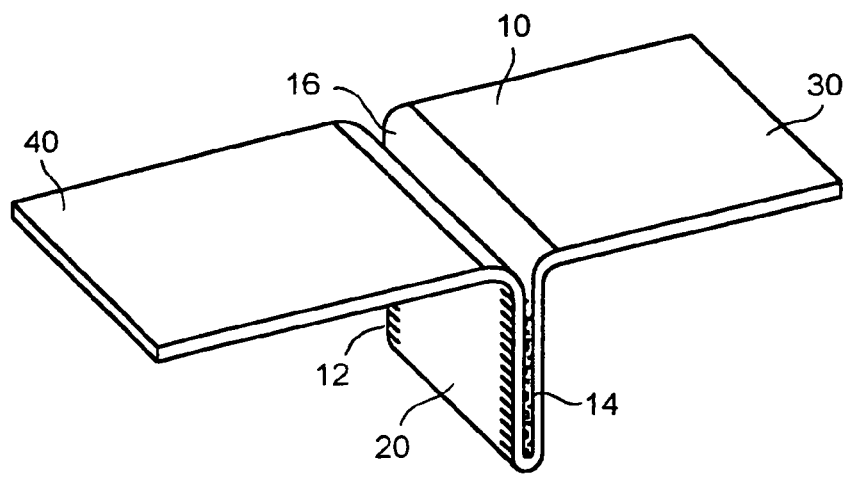
FIG. 1a is a perspective sideview of a first medicament carrier in accordance with the present invention in the closed and perpendicular configuration.

FIG. 1a shows a medicament carrier in the closed configuration comprising an elongate strip 10 having a first and second portion which are folded towards each other until contact is made. A pouch 20 is formed by sealing the two outside edges 12 and 14 of the elongate strip and the third edge 16 is sealed to provide a sealed medicament carrier after introduction of the medicament. The ends of the first and second portions then define a pair of pull release tabs 30 and 40 as shown. The contents of the pouch 20 are released by pulling the pull release tabs 30 and 40 in an opposite direction, either manually or by an automatic releasing means so that the medicament carrier is then in the open configuration as shown in FIG. 1b.

Figure 1B:
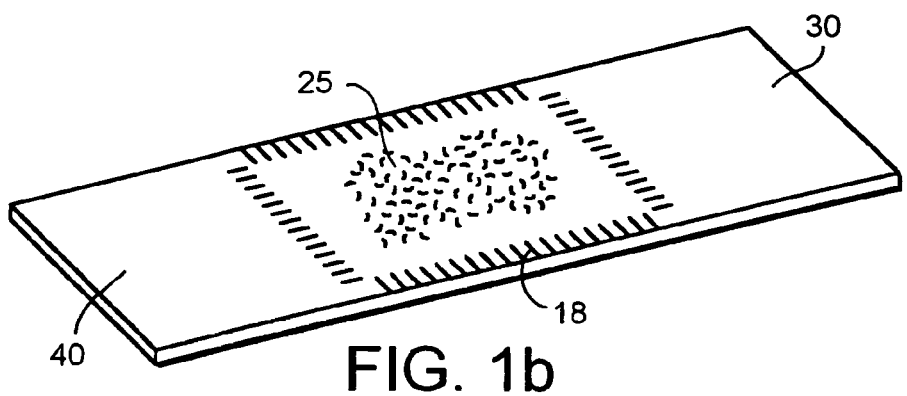
FIG. 1b is a perspective sideview of the first medicament carrier in accordance with the present invention in the open configuration.

FIG. 1b shows the medicament carrier in the open configuration wherein the pair of pull release tabs 30 and 40 have been sufficiently peeled in order to break the seal 18 around the periphery of the pouch 20 thereby exposing the medicament 25 powder contained therein.

Figure 1C:
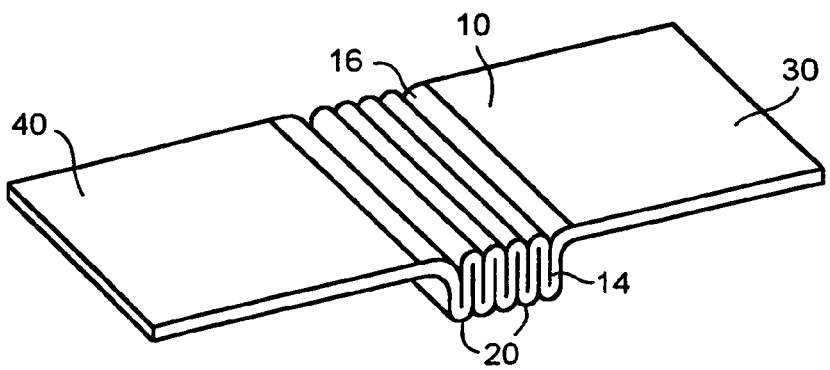
FIG. 1c is a perspective sideview of a second medicament carrier in accordance with the present invention in the closed and perpendicular configuration.

FIG. 1c shows a second medicament carrier in the closed configuration comprising an elongate strip 10 having a first and second portion folded towards each other to form multiple folds. A pouch 20 is formed by sealing the outside edges 14 of each fold and edge 16 to provide a sealed medicament carrier. The ends of the first and second portion define pull release tabs 30 and 40.

Figure 1D:
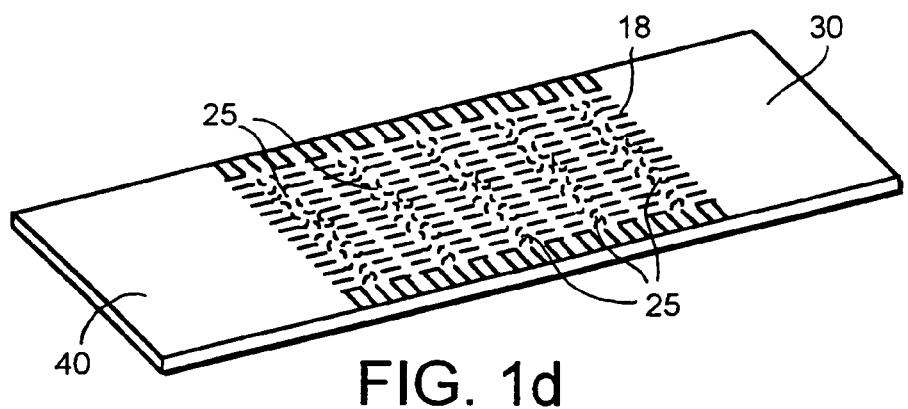
FIG. 1d is a perspective sideview of the second medicament carrier in accordance with the present invention in the open configuration.

The medicament carrier of FIG. 1c is shown in the open configuration in FIG. 1d wherein seals 18 have been broken by pulling the pull release tabs 30 and 40 in an opposite direction to release the medicament 25 powder contained therein.

Figure 1E:
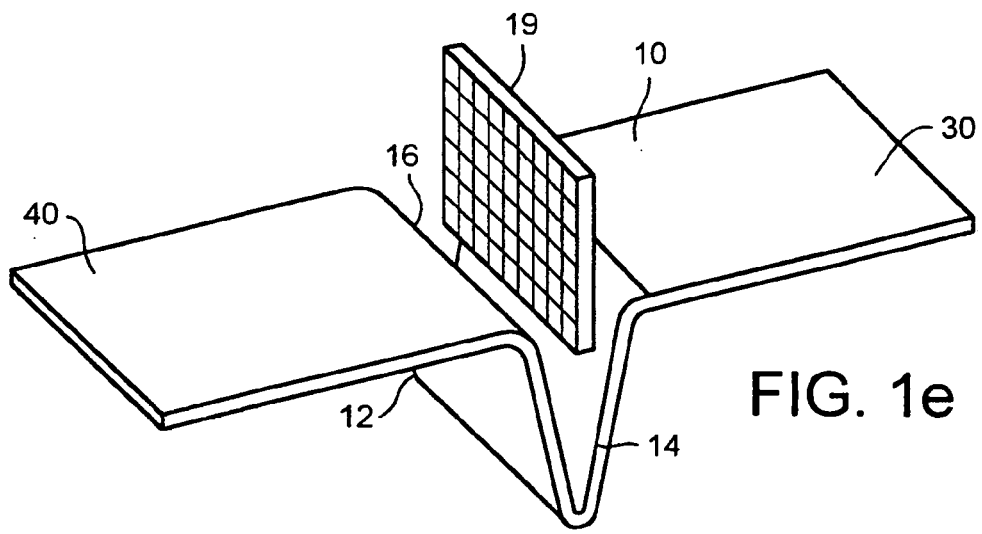
FIG. 1e is a perspective sideview of a third medicament carrier in accordance with the present invention containing a retainer.

FIG. 1e shows a third medicament carrier comprising an elongate strip 10 having a first and second portion in the open configuration into which medicament entrapped on an inert mesh 19 is being added. A pouch (not shown) is formed on joining the two outside edges 12 and 14 of the elongate strip and the third edge 16 to provide a sealed medicament carrier. The contents of the pouch are released by pulling on the two release tabs 30 and 40 in an opposite direction.

Figure 1F:
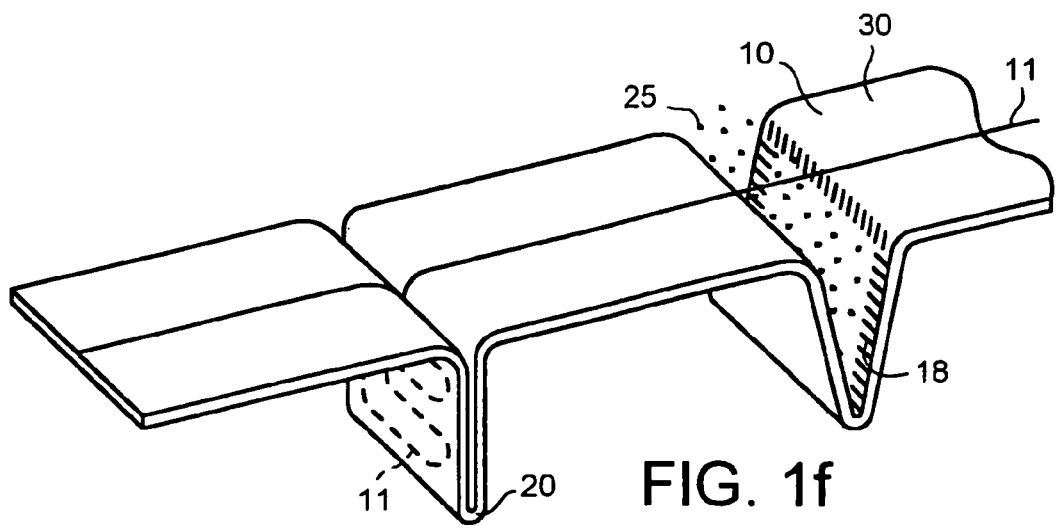
FIG. 1f is a perspective sideview of a fourth medicament carrier in accordance with the present invention illustrating a draw-string opening mechanism in the closed and open configuration.

FIG. 1f shows a fourth medicament carrier in both the open and closed configurations having a drawstring opening mechanism. A drawstring 11 runs down the centre of the elongate strip 10 and is positioned within pouch 20 where it is embedded within medicament 25 in a convoluted configuration. On pulling tab 30 and drawstring 11, seal 18 is broken and the medicament 25 within pouch 20 is released, the physical uncoiling of the drawstring facilitating this release.

Figure 2A:
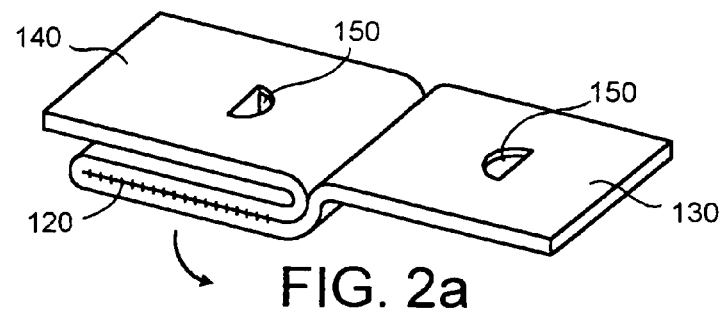
FIG. 2a is a perspective sideview of a fifth medicament carrier in accordance with the present invention in the closed flat configuration.

FIG. 2a shows a fifth medicament carrier wherein the pair of pull release tabs 130 and 140 both possess a perforation 150 enabling it to be connected to a release mechanism incorporated within an inhalation device, or for receipt of finger in manual release. Semi-circumferential cuts are made in the carrier which is then folded back on itself to give the D-shaped perforations 150 shown, thereby avoiding problems associated with debris from the cut material. The medicament pouch 120 lies flat along the elongate strip minimising the amount of space taken up by the medicament carrier when incorporated into an inhalation device.

Figure 2B:
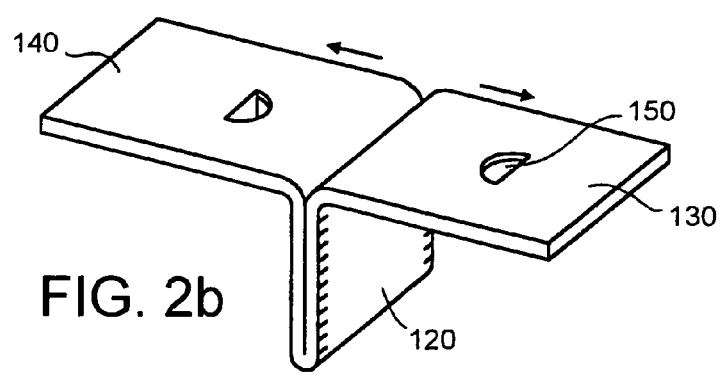
FIG. 2b is a perspective sideview of the fifth medicament container in accordance with the present invention in the closed and perpendicular configuration.

FIG. 2b shows the medicament carrier of FIG. 2a wherein the medicament pouch 120 is in the closed and perpendicular position ready for use. Exposure of the contents of the pouch 120 is achieved by pulling the pair of release tabs 130 and 140 in the direction shown.

Figure 3:
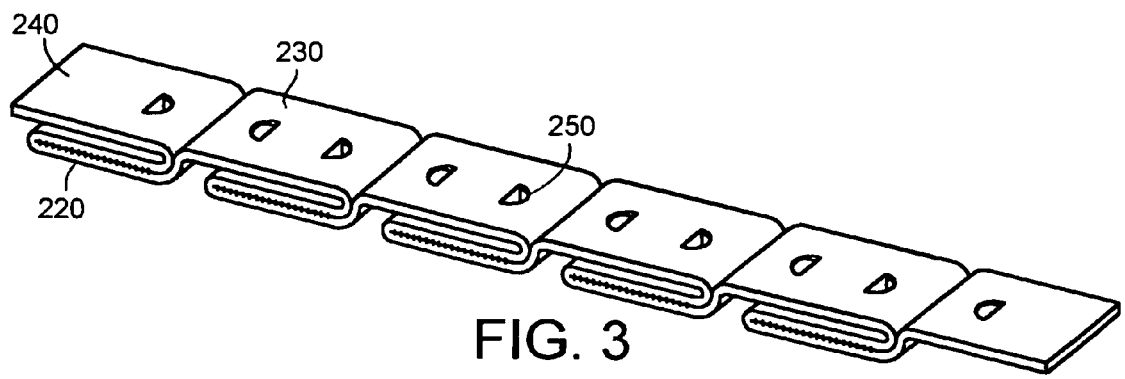
FIG. 3 is a perspective sideview of a fifth medicament carrier in accordance with the present invention in a multi-dose form.

FIG. 3 shows a fifth medicament carrier in a multi-dose form. The multi-dose medicament carrier is formed from an elongate strip incorporating a number of first and second portions, each forming a medicament pouch 220. The individual medicament pouches are shown here in the closed flat configuration. Exposure of the pouch contents is achieved by pulling the pair of release tabs 230 and 240 in an opposite direction.

Figure 4A:
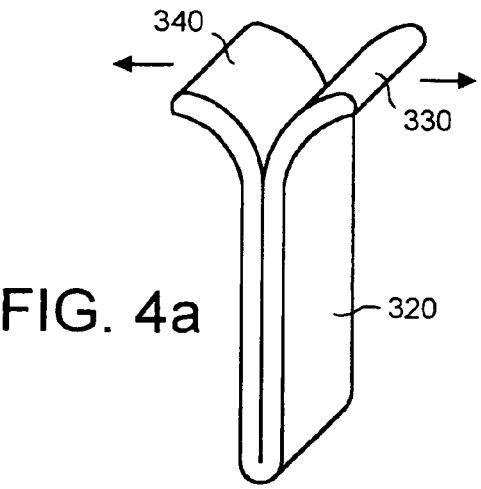
FIG. 4a is a perspective sideview of a sixth medicament carrier in accordance with the present invention in the closed and perpendicular configuration.
Figure 4B:
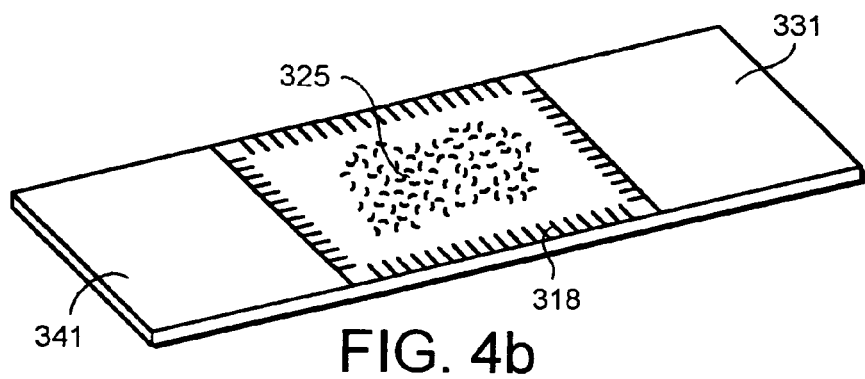
FIGS. 4b, 4c and 4d are perspective sideviews of the sixth medicament carrier in accordance with the present invention in the open configuration.
Figure 4C:
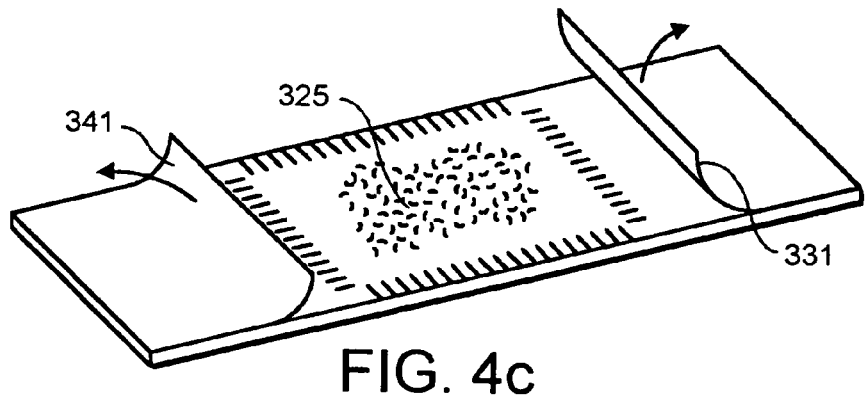
Figure 4D:
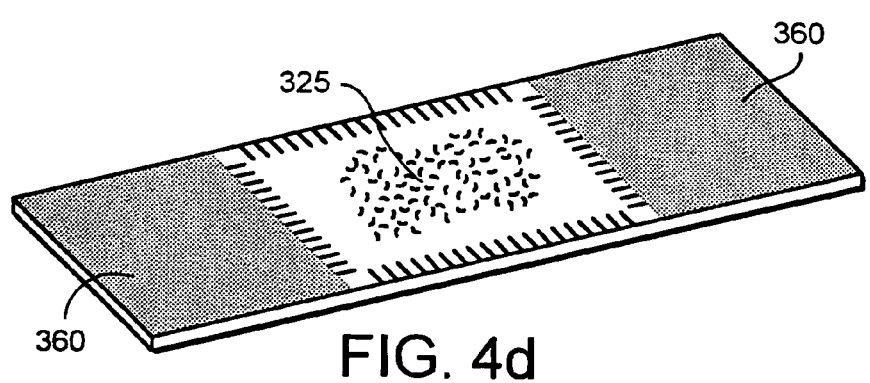

FIG. 4a shows a sixth medicament carrier in the closed and perpendicular position. Pulling the pair of release tabs 330 and 340 in the direction shown breaks the seal around the periphery of pouch 320 thus exposing medicament 325 cream contained therein (FIG. 4b). In the embodiment shown, covers 331 and 341 overlay tabs 330 and 340, and are removable by peeling in the direction indicated in FIG. 4c. Adhesive 360 is exposed on removal of covers 331, 332. The medicament carrier may now be affixed directly on to a patient's skin, being secured by adhesive 360, thereby enabling administration of medicament 325 cream to the patient. Suitable topical medicaments include those for the treatment of acne, eczema, psoriasis and pruritus (e.g., erythromycin and corticosteroids such as fluticasone propionate, clobetasol propionate and alclometasone dipropionate), fungal mycoses (e.g., flucytosine, amphotericin B, oxiconazole nitrate) and viral infections (e.g., aciclovir, zanamivir).

Figure 5A:
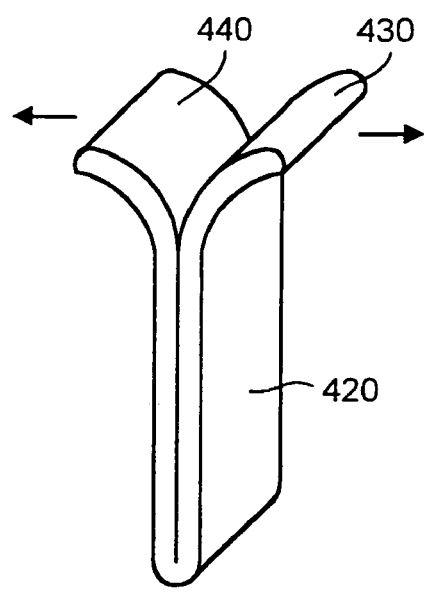
FIG. 5a is a perspective sideview of a seventh medicament carrier in accordance with the present invention in the closed and perpendicular configuration.
Figure 5B:
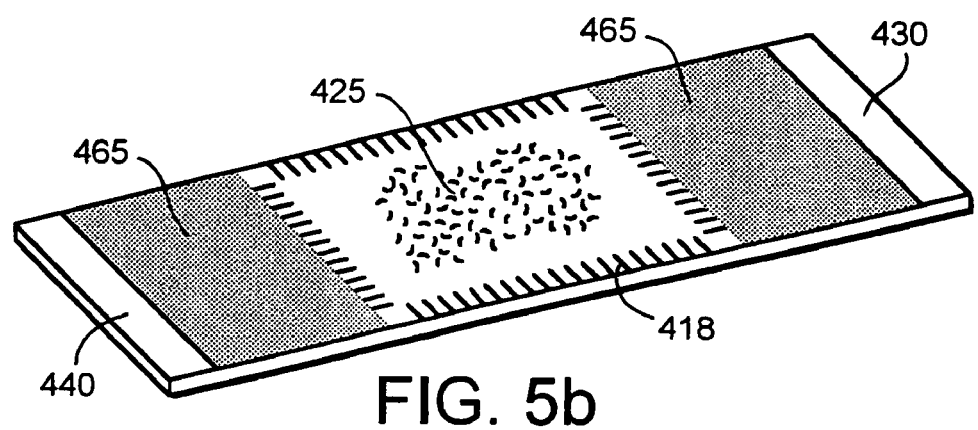
FIG. 5b is a perspective sideview of the seventh medicament carrier in accordance with the present invention in the open configuration.

FIGS. 5a and b show a seventh medicament carrier in the perpendicular and closed position. Medicament 425 cream contained in pouch 420 is exposed on pulling tabs 430 and 440 in the direction shown, thereby rupturing seal 418 (FIG. 5b). Adhesive 465, which does not bond to itself, may now be used to secure the carrier to a patient's skin, thereby facilitating administration of medicament 425 cream to the patient.

Standard methods of filling and sealing the medicament container may be used and form another aspect of the present invention. Such methods include entering a hollow, or a number of hollow, pins into a powder bed so that a defined quantity of powder is taken up into the or each pin. The pin, or number of pins, is then positioned above the individual medicament containers and the powder contained therein released by means of a piston. On removal of the pin, or pins, the medicament containers are sealed so that the powder is contained in a medicament container defined by the two portions of the elongate strip.

Suitable methods of sealing the medicament carrier include the use of adhesives, staples, stamps, pressure and welding methods selected from hot metal welding, radio frequency welding, laser welding and ultrasonic welding. Such sealing techniques may be used to form a suitable join around the periphery of the medicament pouch or pocket which is capable of being peeled away by the patient or by a suitable release mechanism in a controlled manner when in use. The release mechanism may be designed to confer a mechanical advantage, thereby reducing the operating force required to break the seal.

Although not directly relevant to the present invention, it should be noted that medicaments suitable for administration by an inhalation device using the present invention are any drug particles suitable for delivery to the bronchial or alveolar region of the lung which have an aerodynamic diameter of less than 10 micrometers. Larger particles may be used if delivery to other portions of the respiratory tract is desired, such as the mouth or throat. Such medicaments may be selected from a wide range of powdered medicaments and may be in amorphous or crystalline form and may have been comminuted, e.g. ground, and, if necessary, classified and sieved, e.g. on an air jet sieve, to obtain a suitable size or may have been made by direct crystallisation to the desired size.

The medicament carrier herein is suitable for containing medicament, such as those for the treatment of ulcers, e.g., omeprazole, lansoprazole, lipid levels, e.g., simvastatin, atorvastatin, hypertension, e.g., amlodipine, depression, e.g. fluozetine, paroxetine, sertraline, allergies, e.g., loratidine, and psychosis, e.g., olanzapine.

In particular, the medicament carrier is suitable for containing medicament for the treatment of respiratory disorders. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate, ciclesonide or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol or 4-hydroxy-7-[2-[[2-[[3-(2-phenylethoxy)propyl]sulfonyl]ethyl]amino]ethyl-2(3H)-benzothiazolone; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferred medicaments are selected from albuterol, salmeterol, ipratropium bromide, fluticasone propionate and beclometasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an antiinflammatory steroid such as a beclomethasone ester (e.g., the dipropionate) or a fluticasone ester (e.g., the propionate). A particularly preferred combination comprises salmeterol xinafoate salt and fluticasone propionate.

It may be appreciated that any of the parts of the medicament carrier which contact the medicament may be coated with materials such as fluoropolymer materials which reduce the tendency of medicament to adhere thereto. Suitable fluoropolymers include polytetrafluoroethylene (PTFE) and fluoroethylene propylene (FEP).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims or may include, by way of example and without limitation, one or more of the following claims:

The invention claimed is:

1. A carrier comprising a single elongate strip having
   a first portion defining a first end and
   a second portion defining a second end, wherein the first portion and second portion are different areas of a single ribbon which makes up the elongate strip;
   a fold between said first portion and said second portion such that the first portion contacts the second portion; and
   a join between the first portion and the second portion, wherein said join and the fold form the edges of a closed pocket or pouch for containment of medicament, said pocket or pouch containing a unit dose of medicament therein and, wherein said first end and said second end of the elongate strip form a pair of pull release tabs, each of said release tabs having at least one perforation formed therein.

2. A carrier according to claim 1, wherein said pocket or pouch comprises folds therein.

3. A carrier according to claim 1, wherein said pocket or pouch comprises contours or ridges therein.

4. A carrier according to claim 1, additionally comprising a retainer within the pocket or pouch for retaining product thereon.

5. A carrier according to claim 1, wherein each of the ends of the elongate strip has a non self-binding adhesive portion.

6. A carrier according to claim 1, wherein each of the ends of the elongate strip has a peelable cover thereon.

7. A carrier according to claim 6, wherein removal of said peelable cover reveals an adhesive portion on each of the ends of the elongate strip.

8. A carrier according to claim 1, comprising at least one further join forming at least one further pocket or pouch for containment of medicament.

9. A carrier according to claim 1, wherein the ends of the elongate strip form a pair of pull release tabs.

10. A carrier according to claim 9, wherein each of said pull release tabs is shaped for ease of grip.

11. A carrier according to claim 9, wherein each of the pull release tabs has a looped end.

12. A carrier according to claim 9, wherein each of the pull release tabs has at least one perforation therein.

13. A carrier according to claim 1, additionally comprising a drawstring opening mechanism.

14. A carrier according to claim 13, additionally comprising protruding release ends of said drawstring for opening thereof.

15. A carrier according to claim 1, comprising a plurality of carriers, wherein the carrier is multi-unit.

16. A carrier according to claim 15, wherein each of said plurality of carriers is connected together.

17. A carrier according to claim 16, wherein each of said plurality of carriers is formable from the same elongate strip.

18. A carrier according to claim 17, wherein said strip has a point of weakness between each carrier in said series arrangement.

19. A carrier according to claim 17, wherein each pocket or pouch is foldable to lie flat alongside the elongate strip.

20. A carrier according to claim 1, wherein the elongate strip is flexible.

21. A carrier according to claim 1, wherein the elongate strip comprises material selected from the group consisting of metal foil, an organic polymeric material and paper.

22. A carrier according to claim 21, wherein the strip comprises a laminate.

23. A carrier according to claim 1, wherein the join is formable by a joining method selected from the group consisting of heat, laser, radio frequency, adhesive, staple, stamp, pressure and ultrasonic sealing.

24. A carrier according to claim 1, wherein the join is peelable to enable peelable access to the pocket or pouch.

25. A carrier according to claim 1, wherein said medicament is in dry powder, tablet, liquid, paste, cream or capsular form.

26. A carrier according to claim 1, wherein said medicament is selected from the group consisting of albuterol, salmeterol, ipratropium bromide, fluticasone propionate and beclomethasone dipropionate and salts or solvates thereof and any mixtures thereof.

27. An inhalation device comprising a housing in combination with a medicament carrier as claimed in claim 1.

28. An inhalation device according to claim 27, wherein the inhalation device comprises a release mechanism and the carrier comprises a pair of pull release tabs connected to said release mechanism.

29. An inhalation device according to claim 28, wherein the release mechanism is separable from the housing of the inhalation device.

30. Use of a carrier according to claim 1, for dispensing medicament.

31. Use of a carrier according to claim 30, for applying medicament to skin.

32. Use of a carrier according to claim 31, for the treatment of cuts, abrasions or infections of said skin.

33. Use of a carrier according to claim 30, for dispensing slow-release formulations of medicaments via the skin.

34. Use of a carrier according to claim 30, wherein said medicament is used in the treatment of respiratory disorders.

35. Use of a carrier according to claim 34, wherein the medicament is used in the treatment of asthma.

36. Use of a carrier according to claim 35, wherein said medicament is salbutamol or albuterol.

37. A method of making a carrier comprising forming a fold between a first portion defining a first end and a second portion defining a second end of a single elongate strip such that said first portion contacts said second portion; forming a join between said first portion and said second portion wherein said join and the fold form the edges of an open pocket or pouch for containment of medicament; filling said open pocket or pouch with a unit dose of medicament; and closing said open pocket or pouch by forming a further join providing said first and second ends with a pair of pull release tabs; and providing said tabs with at least one perforation.

38. A method of making a carrier in multi-unit form comprising successive iterations of the method of claim 37 to form a series arrangement of a plurality of carries.

* * * * *